US012810750B2

(12) United States Patent
Monaco et al.

(10) Patent No.: US 12,810,750 B2
(45) Date of Patent: Nov. 24, 2026

(54) PORCINE LEAF FAT MEMBRANE USED IN TISSUE MODELS FOR SURGICAL TRAINING AND ASSOCIATED METHODS

(71) Applicant: INTUITIVE SURGICAL OPERATIONS, INC., Sunnyvale, CA (US)

(72) Inventors: Margaret Monaco, Fuquay Varina, NC (US); Joanna Cao, Durham, NC (US); Lucas Tew, Raleigh, NC (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 282 days.

(21) Appl. No.: 18/585,140

(22) Filed: Feb. 23, 2024

(65) Prior Publication Data

US 2024/0290222 A1 Aug. 29, 2024

Related U.S. Application Data

(60) Provisional application No. 63/487,270, filed on Feb. 28, 2023.

(51) Int. Cl.
*G09B 23/30* (2006.01)
*C12N 5/077* (2010.01)

(52) U.S. Cl.
CPC ......... *G09B 23/306* (2013.01); *C12N 5/0653* (2013.01); *C12N 2500/05* (2013.01); *C12N 2500/30* (2013.01); *C12N 2527/00* (2013.01)

(58) Field of Classification Search
CPC .... G09B 23/306; G09B 23/30; C12N 5/0653; C12N 2500/05; C12N 2500/30; C12N 2527/00
See application file for complete search history.

(56) References Cited

U.S. PATENT DOCUMENTS

| | | | | | |
|---|---|---|---|---|---|
| 5,145,452 | A * | 9/1992 | Chevalier ............ | A22C 25/006 452/121 |
| 6,227,202 | B1 * | 5/2001 | Matapurkar ......... | A61K 35/545 128/898 |
| 6,933,103 | B1 * | 8/2005 | Klein .................... | A61L 2/0088 424/572 |
| 8,852,208 | B2 | 10/2014 | Gomez et al. | |
| 9,295,524 | B2 | 3/2016 | Schena et al. | |
| 9,358,074 | B2 | 6/2016 | Schena et al. | |

(Continued)

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — James S. McClellan
(74) *Attorney, Agent, or Firm* — ALLEN, DYER, DOPPELT, + GILCHRIST, P.A.

(57) ABSTRACT

A method for making a porcine leaf fat membrane may include exposing a porcine leaf fat tissue sample to a detergent solution. The porcine leaf fat tissue sample includes a porcine leaf fat membrane and porcine leaf fat connected thereto. The method includes mechanically stripping the porcine leaf fat from the porcine leaf fat membrane after exposing the porcine leaf fat tissue sample to the detergent solution. The porcine leaf fat membrane may be incorporated within a tissue model for surgical training.

11 Claims, 13 Drawing Sheets

(56) References Cited

U.S. PATENT DOCUMENTS

| | | | | |
|---|---|---|---|---|
| 2007/0166397 | A1* | 7/2007 | Katzner | A61K 35/36 424/572 |
| 2013/0130384 | A1* | 5/2013 | Okamoto | C07K 14/78 530/353 |
| 2013/0226314 | A1* | 8/2013 | Li | A61L 31/14 427/2.24 |
| 2018/0344902 | A1* | 12/2018 | Stiefel | A61L 27/58 |
| 2020/0040030 | A1* | 2/2020 | Wang | C07K 1/36 |
| 2020/0286406 | A1* | 9/2020 | Alexander | G09B 23/285 |
| 2020/0397829 | A1* | 12/2020 | Wilhelmi | A61L 27/362 |
| 2023/0295384 | A1* | 9/2023 | Yamago | C08J 5/02 |

* cited by examiner

| Sample Number | PROJECTIONS PER INCH | | | | PROJECTION LENGTH (INCH) | | | | | |
|---|---|---|---|---|---|---|---|---|---|---|
| | 1 | 2 | 3 | AVG | 1 | 2 | 3 | 4 | 5 | AVG |
| 1 | 3 | 3 | 2 | 2.67 | 1.125 | 0.5 | 0.375 | 0.75 | 1.5 | 0.85 |
| 2 | 3 | 2 | 1 | 2.00 | 0.5 | 1 | 0.75 | 0.125 | 0.5 | 0.58 |
| 3 | 3 | 5 | 3 | 3.67 | 0.75 | 0.5 | 0.5 | 0.625 | 0.5 | 0.58 |
| 4 | 4 | 3 | 3 | 3.33 | 0.5 | 0.5 | 2 | 0.25 | 0.75 | 0.80 |
| 5 | 4 | 2 | 2 | 2.67 | 1.25 | 0.25 | 1.75 | 0.75 | 0.625 | 0.93 |
| 6 | 3 | 2 | 3 | 2.67 | 1 | 0.75 | 2 | 0.625 | 0.75 | 1.03 |
| 7 | 2 | 4 | 2 | 2.67 | 3.25 | 0.75 | 2.75 | 1 | 1 | 1.75 |
| 8 | 3 | 3 | 3 | 3.00 | 1.5 | 0.5 | 2 | 0.75 | 1.75 | 1.30 |
| 9 | 2 | 3 | 3 | 2.67 | 2 | 0.75 | 0.5 | 0.5 | 0.375 | 0.83 |
| 10 | 5 | 2 | 3 | 3.33 | 0.75 | 0.75 | 0.625 | 1.25 | 0.375 | 0.75 |
| 11 | 2 | 2 | 2 | 2.00 | 1.375 | 0.5 | 1.375 | 1 | 1.25 | 1.10 |
| 12 | 3 | 1 | 3 | 2.33 | 0.75 | 0.75 | 0.75 | 0.75 | 0.5 | 0.70 |
| 13 | 3 | 3 | 4 | 3.33 | 1 | 0.75 | 0.5 | 0.625 | 1 | 0.78 |
| 14 | 3 | 3 | 2 | 2.67 | 0.5 | 0.75 | 0.375 | 0.5 | 0.5 | 0.53 |
| 15 | 3 | 2 | 3 | 2.67 | 0.5 | 0.5 | 0.5 | 1.875 | 1.25 | 0.93 |
| 16 | 3 | 2 | 3 | 2.67 | 0.5 | 0.375 | 0.625 | 0.625 | 0.375 | 0.50 |
| 17 | 2 | 3 | 3 | 2.67 | 3.5 | 0.5 | 0.5 | 0.375 | 0.5 | 1.08 |
| 18 | 4 | 3 | 2 | 3.00 | 0.75 | 0.5 | 0.75 | 1.125 | 2 | 1.03 |
| 19 | 3 | 1 | 3 | 2.33 | 2 | 1 | 1.5 | 1.25 | 1 | 1.35 |
| 20 | 2 | 2 | 1 | 1.67 | 1 | 0.75 | 0.5 | 0.625 | 4 | 1.38 |
| AVG | | | | 2.70 | | | | | | 0.94 |

FIG. 10

PORCINE LEAF FAT MEMBRANE USED IN TISSUE MODELS FOR SURGICAL TRAINING AND ASSOCIATED METHODS

PRIORITY APPLICATION(S)

This application is based upon provisional Application No. 63/487,270, filed Feb. 28, 2023, the disclosure which is hereby incorporated by reference in its entirety.

FIELD OF THE INVENTION

The present invention relates to the field of surgical training, and more particularly, this invention relates to a porcine leaf fat membrane that may be incorporated into a tissue model for surgical training and related methods.

BACKGROUND OF THE INVENTION

Surgical procedures may be performed using open or general surgery, laparoscopic surgery, and/or robotically assisted surgery. To become qualified to perform surgical procedures, surgeons participate in comprehensive training to become proficient in the variety of tasks required to perform the procedures. Such tasks include inserting and directing surgical tools to anatomical features of interest such as tissue or organs, manipulating tissue, grasping, clamping, cutting, sealing, suturing, and stapling tissue, as well as other tasks. To gain proficiency, it is beneficial to allow surgeons to repeatedly practice these tasks for multiple different procedures. In addition, it can be beneficial to quantify training and performance of such tasks by surgeons, thereby enabling them to track progress and improve performance.

Various surgical training systems have been developed to provide surgical training. For example, training may be conducted on human cadavers. However, cadavers may be expensive and provide limited opportunities to train. In addition, a single cadaver may not allow the surgeon to repeatedly practice the same procedure. Surgical tissue models have also been utilized for surgical training. However, these tissue models may not be suitable for training minimally invasive procedures using laparoscopic or robotically assisted tools. In minimally invasive procedures, the surgical tools are inserted into the body via natural orifices or small surgical incisions and then positioned near the anatomical features of interest.

Harvested porcine tissue has been used to develop surgical training models for use in thoracic and cardiac surgery because the anatomy of the porcine organs and tissue types, such as the heart and lungs, are similar in anatomy to human organs and may mirror the anatomy of the human body. One tissue type that has been challenging to simulate with a surgical training model is the tissue simulation of the human peritoneum membrane such that the cautery, adhesions and physical properties of the simulated peritoneum mirrors that of the peritoneum of human patients.

SUMMARY OF THE INVENTION

This summary is provided to introduce a selection of concepts that are further described below in the Detailed Description. This summary is not intended to identify key or essential features of the claimed subject matter, nor is it intended to be used as an aid in limiting the scope of the claimed subject matter.

A method for making a porcine leaf fat membrane may comprise exposing a porcine leaf fat tissue sample to a detergent solution, the porcine leaf fat tissue sample comprising a porcine leaf fat membrane and porcine leaf fat connected thereto. The method may include mechanically stripping the porcine leaf fat from the porcine leaf fat membrane after exposing the porcine leaf fat tissue sample to the detergent solution.

The detergent solution may be at a temperature in a range of 35° C. to 40° C. and the exposing may be carried out for a time in a range of 3 to 5 minutes. The mechanically stripping may comprise mechanically stripping to form a base porcine leaf fat membrane layer and a plurality of porcine leaf fat membrane projections extending therefrom. The plurality of leaf fat membrane projections may comprise at least 2 projections per square inch and having a length of at least 0.5 inches.

The mechanically stripping may comprise mechanically scraping with an edged tool, and in an example, mechanically scraping with a reciprocal motion. The mechanically scraping may also comprise mechanically scraping with a fluid assist. The porcine leaf fat membrane may be sealed in a resealable bag. A portion of the detergent solution may be added to the bag. The detergent solution may comprise at least one of an anionic and cationic surfactant in an aqueous solution.

A method for making a tissue model for surgical training may comprise exposing a porcine leaf fat tissue sample to a detergent solution, the porcine leaf fat tissue sample comprising a porcine leaf fat membrane and porcine leaf fat connected thereto. The method further includes mechanically stripping the porcine leaf fat from the porcine leaf fat membrane after exposing the porcine leaf fat tissue sample to the detergent solution and incorporating the porcine leaf fat membrane in the tissue model. The method may include incorporating the porcine leaf fat membrane as a substitute for peritoneum in the tissue model.

In an example, a porcine leaf fat membrane may comprise a base porcine leaf fat membrane layer and a plurality of porcine leaf fat membrane projections extending therefrom. The plurality of leaf fat membrane projections may comprise at least 2 projections per square inch and having a length of at least 0.5 inches. The porcine leaf fat membrane may have an elasticity in the range of 4.6 MPa to 20 MPa. A colorant may be added to the leaf fat membrane.

BRIEF DESCRIPTION OF THE DRAWINGS

Other objects, features and advantages of the present invention will become apparent from the Detailed Description of the invention which follows, when considered in light of the accompanying drawings in which:

FIG. 10 is a table showing example dimensions of the porcine leaf fat membrane projections.

DETAILED DESCRIPTION

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

Figure 1:
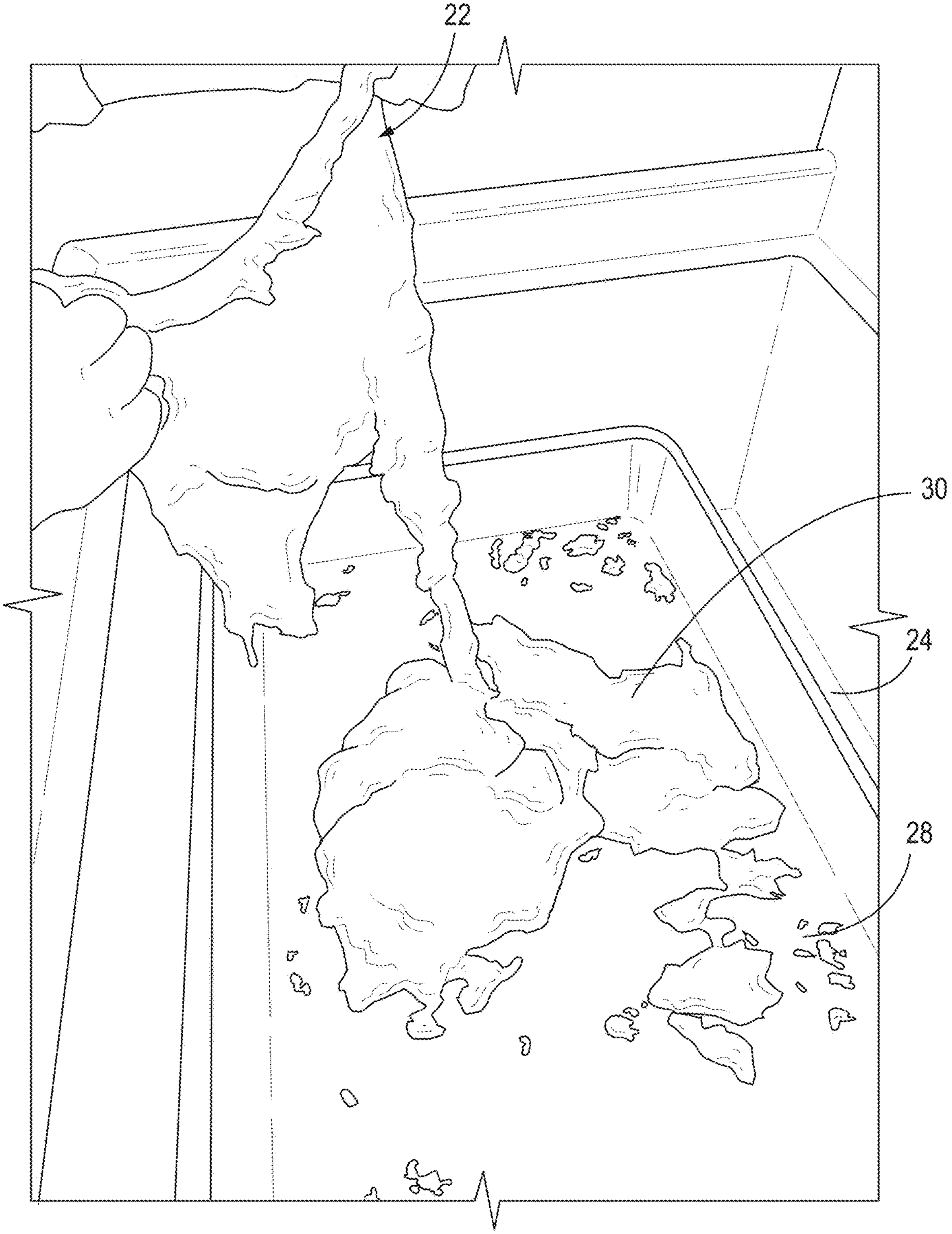
FIG. 1 is an image of a porcine leaf fat tissue sample separated from harvested porcine tissue.
Figure 2:
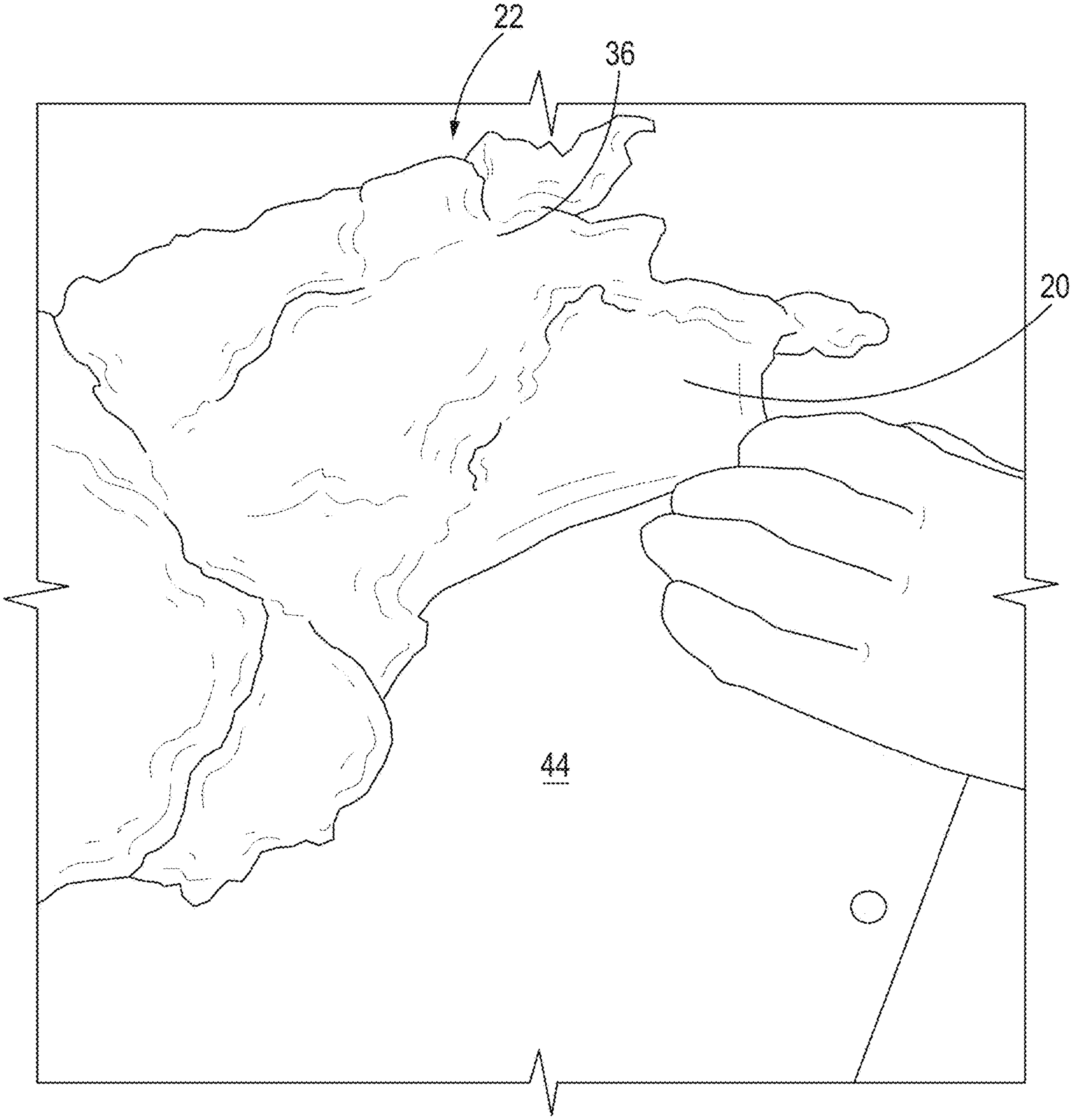
FIG. 2 is another image of the porcine leaf fat tissue sample.

Referring now to the images of FIGS. 1-4, a method for making a porcine leaf fat membrane 20 is illustrated. A porcine leaf fat tissue sample 22 is shown being manually raised in the image of FIG. 1 and had been exposed in a basin 24 to a detergent solution 28. Exposing the porcine leaf tissue sample 22 to the detergent solution 28 allows a portion of the porcine leaf fat tissue sample 22 to unravel or separate from other harvested samples of accumulated porcine tissue 30 that remain in the basin 24. As shown in FIG. 2, the porcine leaf fat tissue sample 22 includes the porcine leaf fat membrane 20 and porcine leaf fat 36 connected thereto, where a portion of the porcine leaf fat has been mechanically stripped from the porcine leaf fat membrane.

Figure 3:
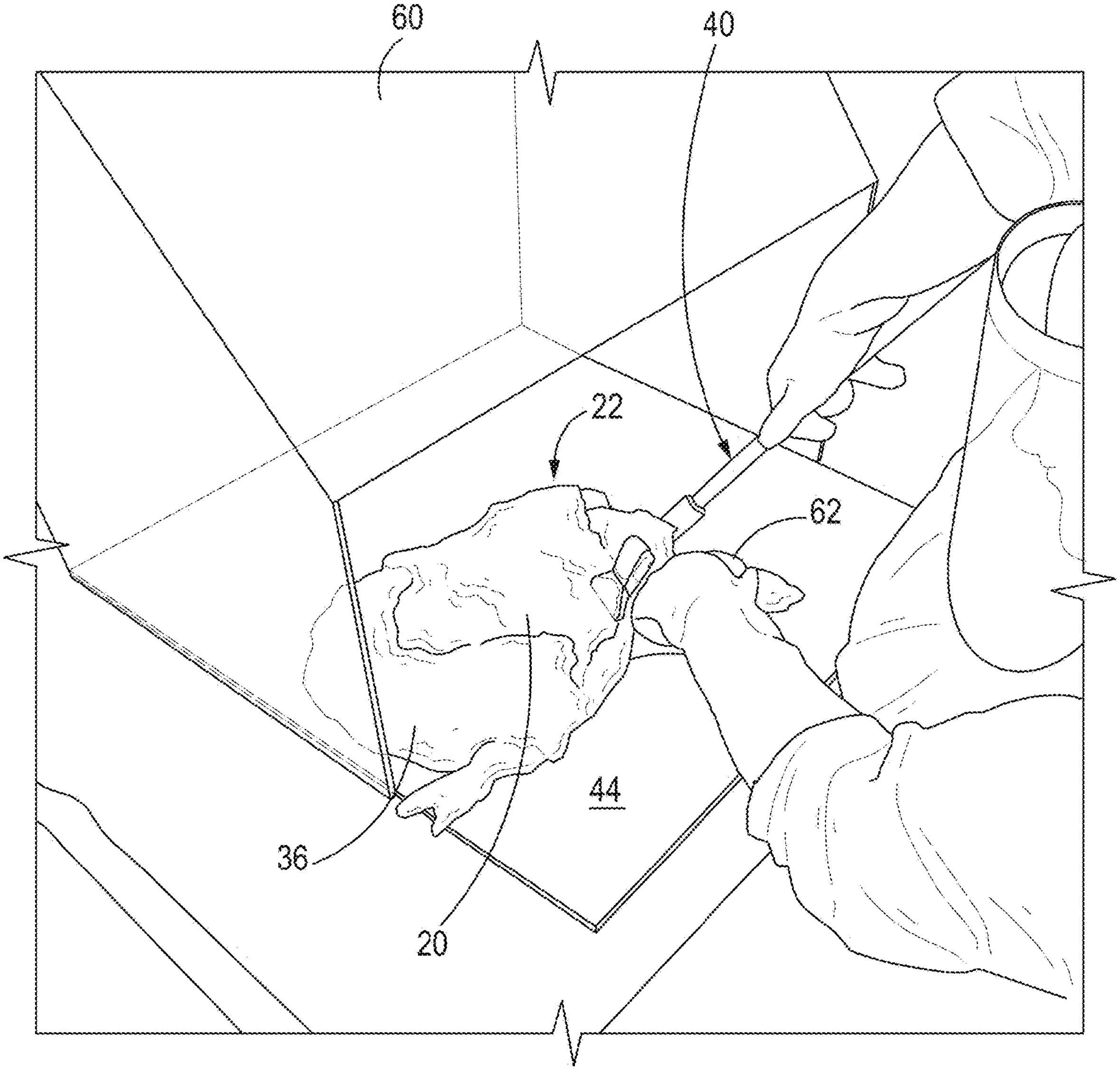
FIG. 3 is an image of mechanically stripping the porcine leaf fat from the porcine leaf fat membrane.
Figure 4:
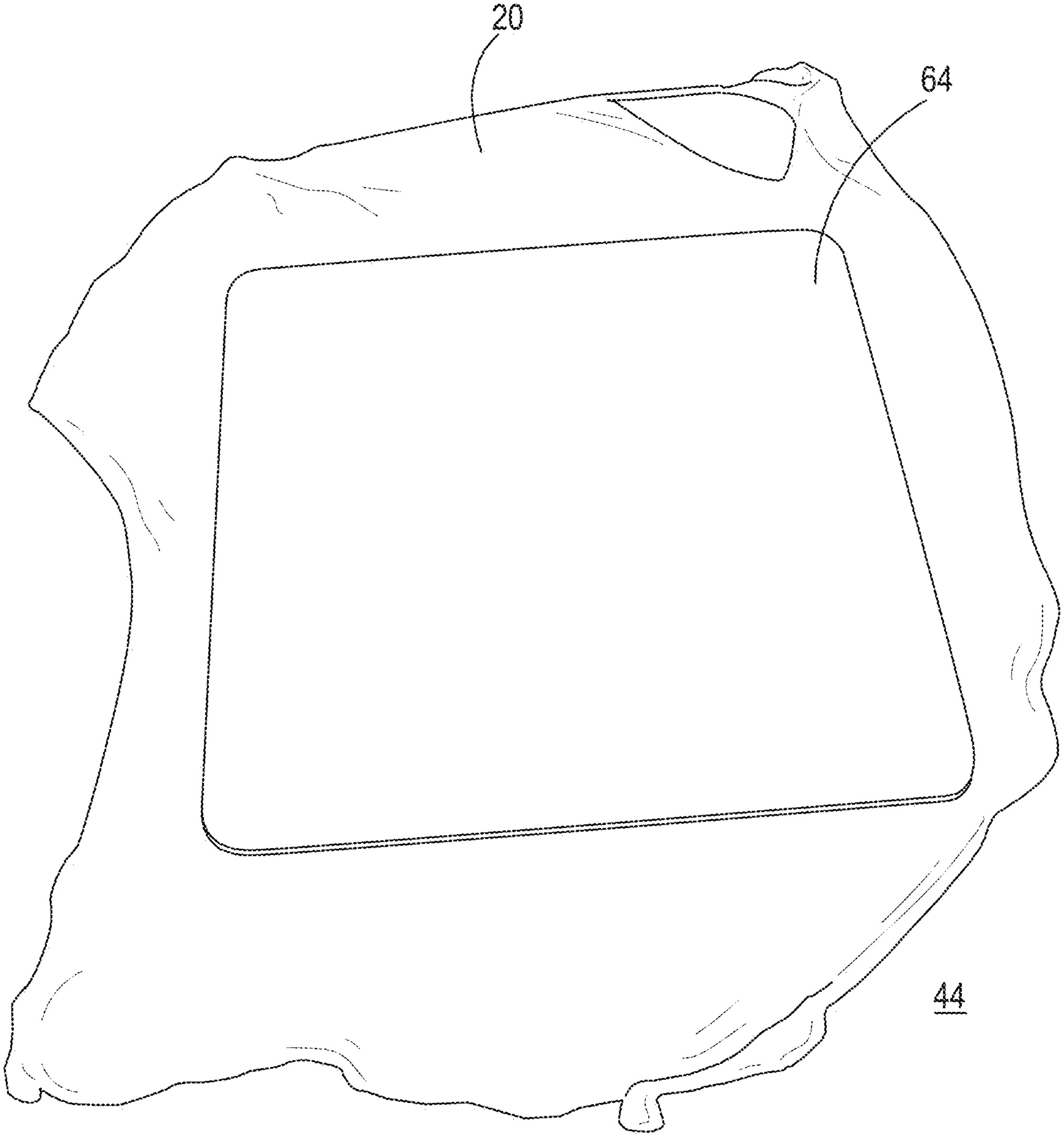
FIG. 4 is an image of the porcine leaf fat membrane positioned under a sizing template.

As explained with reference to FIGS. 2-4, the porcine leaf fat 36 is mechanically stripped from the porcine leaf fat membrane 20 after exposing the porcine leaf fat tissue sample 22 to the detergent solution 28, using in an example an edged tool 40 shown in FIGS. 5 and 6. The edged tool 40 may be used to mechanically scrape the porcine leaf fat 36 from the porcine leaf fat membrane 20 (FIG. 3) using in an example a reciprocal motion. The edged tool 40 may include a fluid assist that passes a fluid such as compressed air that is discharged from the edged tool into the connective junction between the porcine leaf fat 36 and porcine leaf fat membrane 20 as will be explained in greater detail below.

The porcine leaf fat tissue sample 22 that includes the porcine leaf fat membrane 20 and porcine leaf fat 36 connected thereto is harvested from that area of the pig where it forms the soft visceral fat layer that surrounds the kidney of the pig and is often used for different cooking applications. Porcine leaf fat tissue 22 sits posterior to the kidneys and anterior to the pig's spinal column, and protects and insulates the pig's kidneys. Some of those skilled in the art within the porcine food community refer to the porcine leaf fat tissue 22 as the "backfat."

The porcine leaf fat tissue sample 22 shown in the images of FIGS. 1 and 2 includes two separate layers as the porcine leaf fat membrane 20 and porcine leaf fat 36 as connected fat issue. Usually, porcine leaf fat tissue 22 is processed in the food industry by grinding the porcine leaf fat 36 and porcine leaf fat membrane 20 together before adding the combined ground material into different food products. The separation of the porcine leaf fat membrane 20 from the porcine leaf fat 36 is difficult by hand, and usually is not accomplished in the food industry. Instead, the porcine leaf fat tissue 22 is ground for later application to different foods as a naturally sourced product that is lower in saturated fat than many other animal fats and may contain up to 50% of monounsaturated fat without the hydrogenated oils that accompany many industrially processed fats.

In an example, the detergent solution 28 is at least one of an anionic and cationic surfactant in an aqueous solution and used in combination with heat to help loosen the porcine leaf fat 36 from the porcine leaf fat membrane 20. The detergent solution 28 may be heated to a temperature range of about 35° C. to about 40° C., corresponding to a range of human body temperatures. However, this range may vary and depending on the type of detergent solution, the lower temperature may be below 35° C. and the upper temperature may be above 40° C. for the specified range. In the example of the basin 24 shown in FIG. 1, about one tablespoon of detergent may be added to the warm water in the basin.

An example detergent solution 28 that may be employed is a Tide® Free and Gentle Liquid Laundry Detergent in an aqueous solution that includes not only anionic and cationic surfactants when dissolved in the aqueous solution, but also includes other components to help saponify the porcine leaf fat 36 due to the amphiphilic nature of the detergent solution and the enzyme activity of other added components. The detergent solution 28 helps make the porcine leaf fat tissue sample 22 more malleable and loosens the porcine leaf fat membrane 20 from the porcine leaf fat 36. The long hydrocarbon chains making up the lipophilic portion of the detergent solution 28 contact the fatty components in the porcine leaf fat 36 and help form micelles and separate the porcine leaf fat membrane 20 from the porcine leaf fat.

The different detergent solutions 28 that may be used in a variety of forms, including anionic, cationic and non-ionic. For example, anionic detergents may have negatively-charged sulfate groups as the hydrophilic head, while cationic detergents contain a positively-charged ammonium group. The combination of the different molecules forming the detergent solution 28 may constitute active ingredients in a household detergent, such as the example Tide® Free and Gentle Liquid Laundry Detergent. The detergent solution 28 preferably does not include any harsh chemicals that may destroy the porcine leaf fat membrane 20 during exposure to the detergent solution and the subsequent mechanical stripping process.

Different detergent solutions 28 may be employed having different surfactants, such as more commonly used linear or branched anionic sodium alkylbenzene sulfonates. These and other classes of anionic surfactants may be employed that include a hydrophilic sulfonate head-group and hydrophobic alkylbenzene tail group. Other anionic surfactants, such as sodium laureth sulfate and similar branched alkylbenzene sulfonates, may be employed as non-limiting examples. This type of anionic surfactant may be combined with different cationic surfactants, including sodium salts that have a sodium cation and a conjugate base anion such as inorganic or organic acids that form the salt. An example includes sodium salts of C12-C18 fatty acids.

Other components added into the detergent solution 28 in conjunction with a primary surfactant may include sodium citrate as a sodium salt of citric acid, sodium formate as a sodium salt of formic acid, and sodium borate as a salt of sodium with an anion that includes boron and oxygen and possibly hydrogen or any hydrate thereof. The detergent solution 28 may also include different types of hydrotropes that solubilize hydrophobic compounds by a mechanism other than micellar solubilization, and may include hydrophilic and hydrophobic components similar to common surfactants, with the hydrophobic component usually being too small to create spontaneous self-aggregation as compared to typical surfactants.

The detergent solution 28 may include linear or branched polyethylenimine (PEI) having an amine group and aliphatic spacers. Different amine oxides may be incorporated that include a functional nitrogen-oxygen coordinate covalent bond with different hydrogen and/or substituent group side chains. Different enzymes may be incorporated, such as an amylase enzyme that catalyzes the hydrolysis of starch into sugars, and thus, helps loosen the porcine leaf fat membrane 20 from the porcine leaf fat 36. Different mannosidases may be incorporated that help cleave either the alpha or beta form of mannose and aid in separating the porcine leaf fat membrane 20 from the porcine leaf fat 36. Different serine proteases may be used to initiate nucleophilic attacks on peptide bonds, which also help loosen the protein rich porcine leaf fat membrane 20 from the porcine leaf fat 36.

In an example, the detergent solution 28 as noted before may be in the range of about 35° C. to about 40° C. corresponding to a range of human body temperature, which in the example of the harvested porcine leaf fat tissue sample 22, provides the best temperature range for saponification coupled with any enzyme action from various components in the detergent solution 28. That range may vary above and below the stated values as noted before. The exposure of the porcine leaf fat tissue sample 22 to the detergent solution 28 may be carried out for a time necessary to help loosen and separate the porcine leaf fat membrane 20 from the porcine leaf fat 36 and depends on the type and strength of the detergent solution. In an example, a time range of about 3 to 5 minutes exposure using the example Tide® Free and Gentle Liquid Laundry Detergent has been found adequate. However, that range may vary and the time period may vary with a lower exposure time below 3 minutes and a greater exposure time above 5 minutes.

It is possible to place 10 porcine leaf fat tissue samples 22 into the basin 24 for initial exposure to the detergent solution 28, followed by removing individual porcine leaf fat tissue samples 22 from the basin such as shown by the porcine leaf fat tissue sample 22 held vertically in the image of FIG. 1. Only one porcine leaf fat tissue sample 22 is shown as having been exposed to a detergent solution in the image of FIG. 1.

As shown in the image of FIG. 2, after removal from the basin 24, the porcine leaf fat tissue sample 22 is placed onto a preparation table 44 or similar work bench with the porcine leaf fat membrane 20 facing down against the upper surface of the preparation table. The image of FIG. 2 further shows a small section of the porcine leaf fat 36 has already separated from the porcine leaf fat membrane 20. Once the porcine leaf fat tissue sample 22 is positioned in place on the preparation table 44, and a small section of the porcine leaf fat 36 separated from the porcine leaf fat membrane 20, the porcine leaf fat 36 is mechanically stripped from the porcine leaf fat membrane 20 by mechanically scraping with the edged tool 40 using a reciprocating motion in a non-limiting example.

Figure 5:
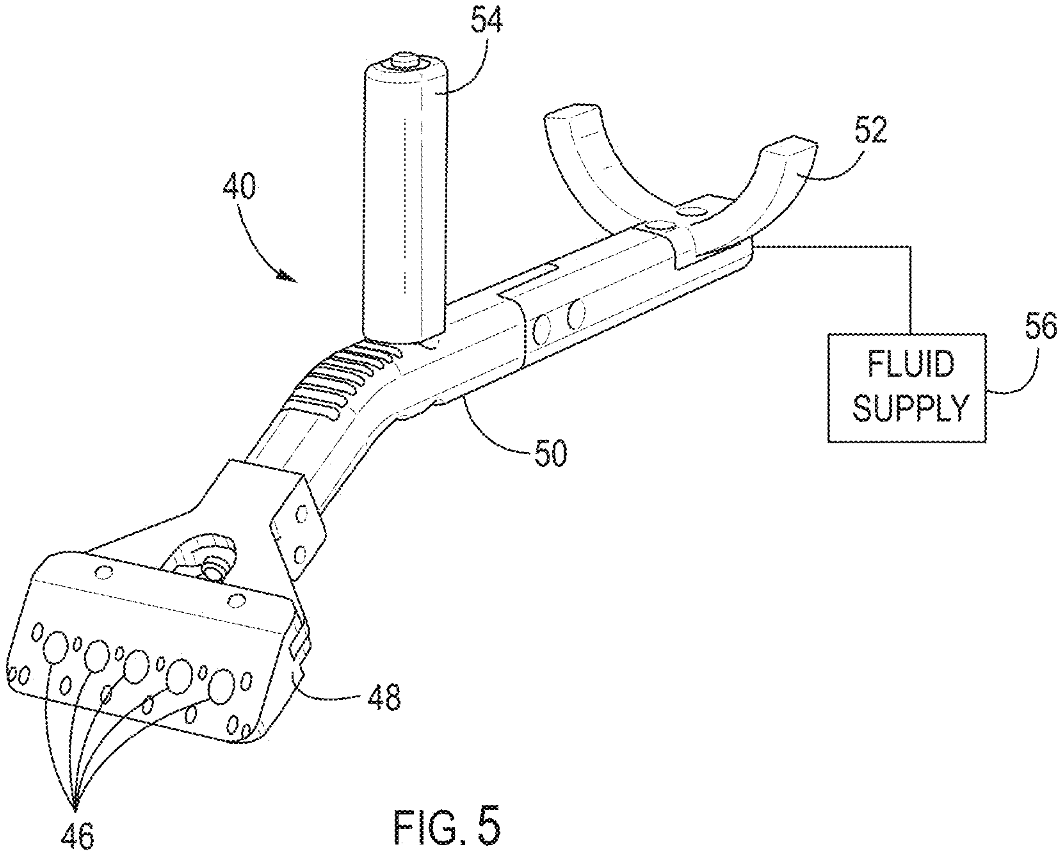
FIG. 5 is an isometric view of an edged tool that may be used for mechanically stripping the porcine leaf fat from the porcine leaf fat membrane.
Figure 6:
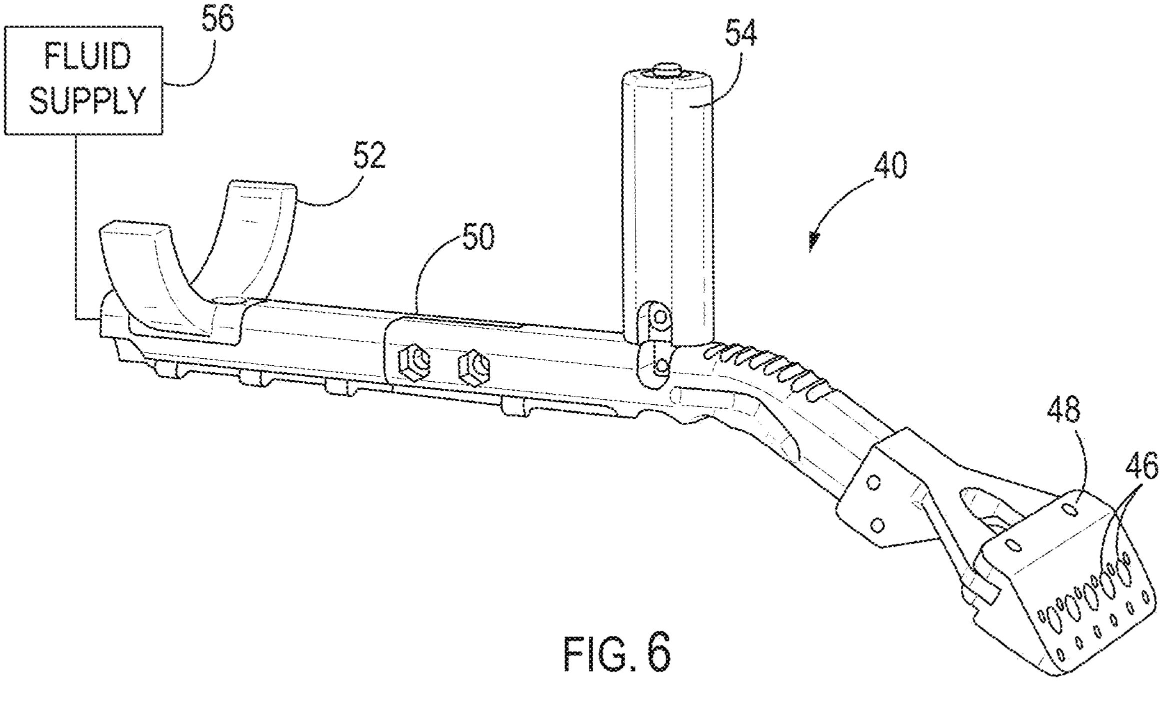
FIG. 6 is another isometric view of the edged tool shown in FIG. 5.

An example of an edged tool 40 is a scraper shown in FIGS. 5 and 6 that may include a fluid assist mechanism by delivering a fluid such as compressed air through orifices 46 located at the edge of a nozzle head 48 carried by a support handle 50. The support handle 50 is configured with an arm rest 52 on which a user rests their forearm and a handle grip 54 that is grasped by a user. This configuration of the edged tool 40 helps the user or other technician avoid repetitive motion injuries as the user manipulates and moves the edged tool back-and-forth while applying a strong downward force. This configuration of the edged tool 40 also allows the user to apply more downward force to the tapered edge of the nozzle head 48 and push the porcine leaf fat 36 from the porcine leaf fat membrane 20. A supply of fluid 56 may be connected to the end of the support handle 50 to provide a fluid such as compressed air through the support handle and through the orifices 46 in the nozzle head 48 and assist in the porcine leaf fat membrane 20 separation.

It is useful to mechanically strip the porcine leaf fat membrane 20 from the porcine leaf fat tissue sample 22 under an enclosed hood 60 (FIG. 3) to minimize cleanup. The technician or user may employ a magnet 62 to help hold the porcine leaf fat sample 22 against the preparation table 44 as illustrated by the user in FIG. 3 who is shown exerting downward pressure onto the magnet and against the porcine leaf fat membrane to hold it secure against the preparation table 44 during the mechanical stripping. The preparation table 44 in this example would be formed of a magnetic material to allow the magnet 62 to exert its magnetic force. Use of the magnet 62 to hold down the porcine leaf fat tissue sample 22 while mechanically stripping under the enclosed hood 60 helps limit the splatter of the porcine leaf fat 36 during stripping and limit clean-up time. Although a use of a magnet 62 has been described, other mechanisms may be used to hold the porcine leaf fat sample 22 against the preparation table 44 such as clamps, a weight, or other hold down mechanism. Although using the compressed air or other fluid to assist in the mechanical stripping may not be necessary, it may be helpful in some circumstances.

Usually, a reciprocating, back-and-forth motion may be used when manually operating the edged tool 40 to strip the porcine leaf fat membrane 20 from the porcine leaf fat 36. Once the porcine leaf fat membrane 20 is stripped from the porcine leaf fat 36, it may be sealed in a resealable bag with a portion of the detergent solution 28 added to the bag for storage. If the porcine leaf fat membrane 20 is to be used immediately after it has been mechanically stripped from the porcine leaf fat 36, it may be cut to size using a template 64 as shown in the image of FIG. 4. A technician may employ a knife or other cutting tool to cut around the template 64 and cut the porcine leaf fat membrane 20 to a desired size based on the size of the template. The template 64 may be configured to cut specific porcine leaf fat membrane 20 shapes and sizes for specific end use applications, such as creating a recto-prosthetic fold in a tissue model or simulating a human peritoneum membrane in a tissue model.

Figure 9:
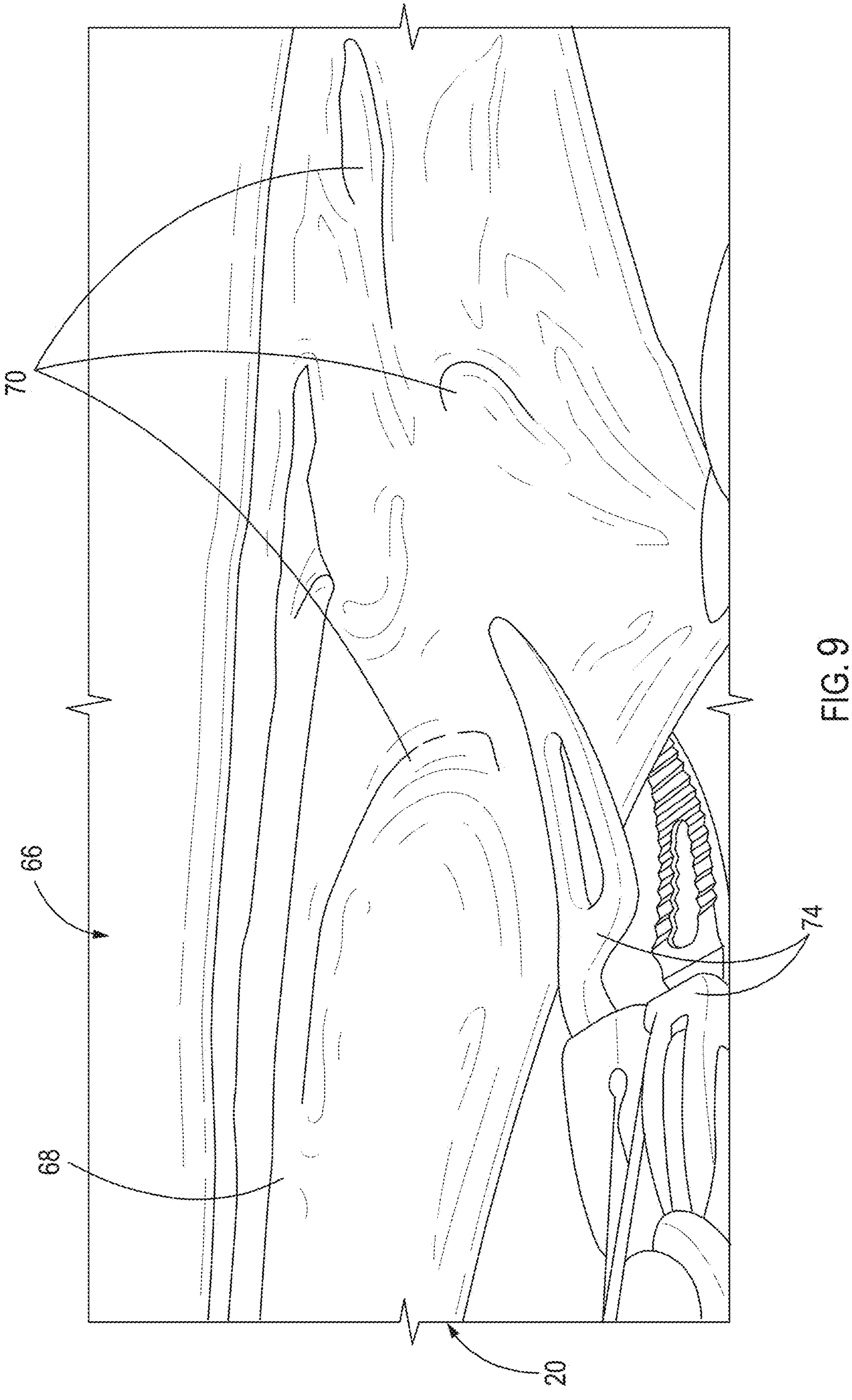
FIG. 9 is an image of the base porcine leaf fat membrane layer and showing a plurality of porcine leaf fat membrane projections extending therefrom.

The method for making the porcine leaf fat membrane 20 as described prepares a porcine leaf fat membrane that may be used in an advanced tissue model for surgical training as shown by the image's upper portion at 66 in FIG. 9 to which the porcine leaf fat membrane 20 is attached. The porcine leaf fat membrane 20 has excellent crosswise stretch and elasticity that permits it to be manipulated into many different contours of different components making up a tissue model 66, for example, a surgical training model that may include a simulated human prostate or thoracic tissue and may include a simulated peritoneum membrane. The porcine leaf fat membrane 20 has excellent moisture content that helps in surgical training when using cautery techniques and prevents underlying and adjacent tissues from drying out quickly. The elasticity of the porcine leaf fat membrane 20 may vary depending on how it had been mechanically stripped. The elasticity can be measured based on the stiffness of the membrane and be measured based upon elastic modulus, i.e., Young's modulus of the material and range from 4.6 MPa to 20 MPa.

Figure 7:
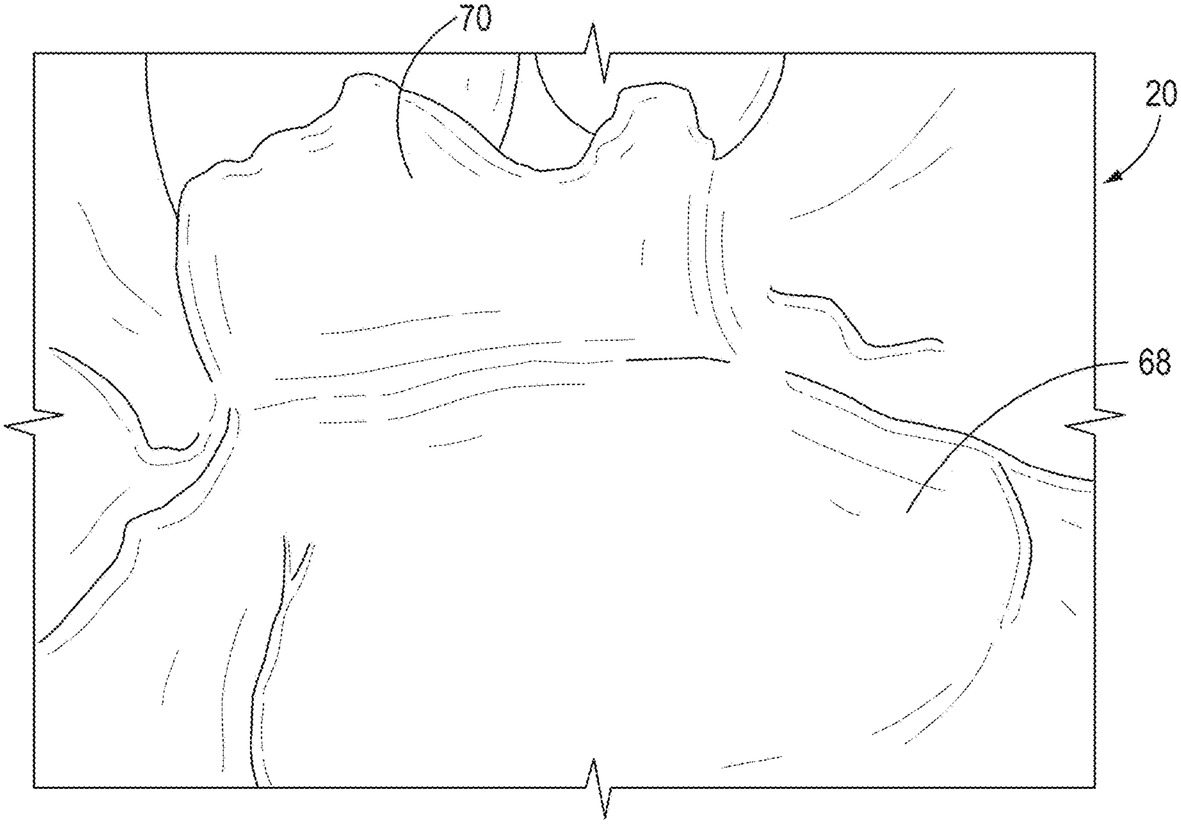
FIG. 7 is an enlarged image of a leaf fat membrane projection extending from a base porcine leaf fat membrane layer.
Figure 8:
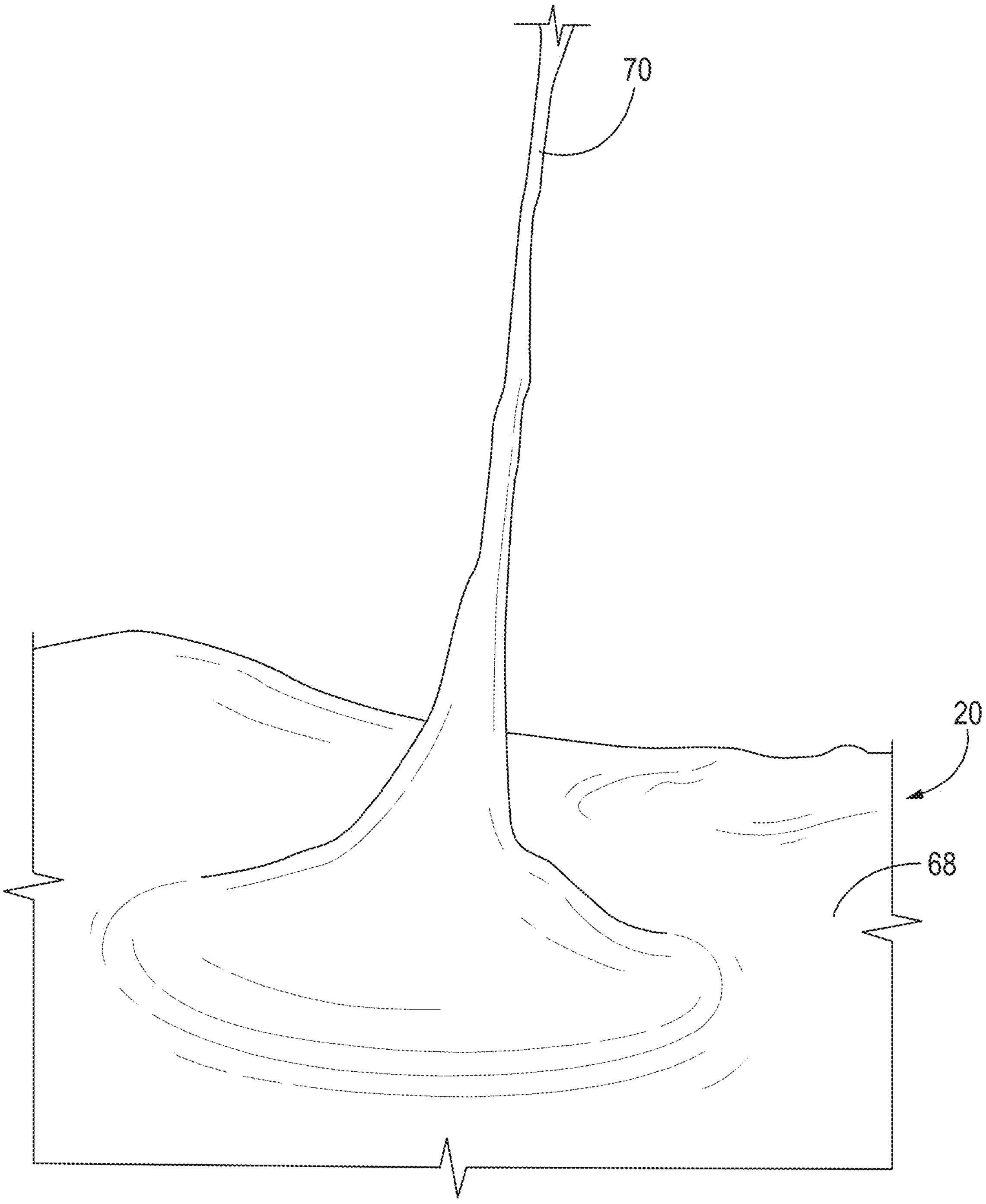
FIG. 8 is another image of a porcine leaf fat membrane projection.

As shown in the images of FIGS. 7-9, when mechanically stripping the porcine leaf fat 36 from the porcine leaf fat membrane 20, a base porcine leaf fat membrane layer 68 is formed as part of the porcine leaf fat membrane and has a plurality of porcine leaf fat membrane projections 70 extending therefrom that form a stringy texture on the surface of the base porcine leaf fat membrane layer 68, which was once attached to the porcine leaf fat 36. These projections 70 may be formed and vary in configuration and length by varying the type of manual stroke applied to the edged tool 40 when mechanically stripping the porcine leaf fat membrane 20 from the porcine leaf fat 36 or when using another mechanical stripping mechanism.

The plurality of leaf fat membrane projections 70 may be at least about two (2) projections per square inch and have a length of at least about 0.5 inches. These leaf fat membrane projections 70 form the stringy texture on the porcine leaf fat membrane layer 68 that aids in attaching or suspending different components of the tissue model 66. For example, when simulating the peritoneal membrane, the projections 70 may help hold and stabilize other harvested porcine components forming the tissue model 66. There may be a variation in the lengths and types of the leaf fat membrane projections 70 on the porcine fat membrane layer 68 and may have a variation in color intensity. This variation of color may be due to the structure of the leaf fat membrane projections 70 that are largely protein based and highly reactive to dyes used to color the different portions of the tissue model 66.

An example of a leaf fat membrane projection 70 is shown in the image of FIG. 7 where the projection is shown formed as a longitudinal extending, thin vertical membrane. Another view (FIG. 8) shows the thin upper portion of the projection 70 supported by a pyramidal base. The image of FIG. 9 shows the porcine leaf fat membrane 20 incorporated into a tissue model 66 shown by the image's upper portion to which the porcine leaf fat membrane is attached, which may correspond to other simulated organs and tissue components. Different leaf fat membrane projections 70 are shown on the porcine fat membrane layer 68. In this example, the porcine leaf fat membrane 20 is being pulled from the tissue model 66 to which it is attached using a mechanical tissue clamp 74. An example dye is a RIT dye that has an affinity for the protein structure of the leaf fat membrane 20. Although the leaf fat membrane 20 is primarily formed from proteins, there still remains some fat content, which gives a natural color variation with the proteins when dyed.

The projections 70 may extend out from and/or be embedded within the base porcine leaf fat membrane layer 68 as part of the porcine leaf fat membrane 20. The porcine leaf fat membranes 20 produced according to the process described herein may include projections 70 that have been elongated and/or with increased distribution density. In some examples, some projections 70 may be preserved to substantially match their initial state before processing. Porcine leaf fat membranes 20 produced according to the process described herein may also have superior adhesive properties when compared to traditional methods, and such improvement may be attributed to the projections 70 within the membranes, which may be elongated, rearranged, or preserved.

In simulated surgery using the tissue model 66, the use of the porcine leaf fat membrane 20 helps provide surgeons with a realistic surgical experience to build their skills in a safe learning environment. The porcine leaf fat membrane projections 70 aid in this objective by accurately simulating adhesions of the human peritoneum membrane to underlining simulated organ structures formed with harvested porcine tissue. Because these adhesions formed by the leaf fat membrane projections 70 help simulate a realistic human peritoneum, surgeons under training can learn how to dissect membrane apart using a combination of blunt dissection, cautery, and manual cutting. An adhesive may applied to the porcine leaf fat membrane 20 to help adhere the leaf fat membrane and the projections 70 to other simulated organ structures.

The table of FIG. 10 shows an example of the number of projections 70 per square inch and projections per length based on 20 different samples, and showing an average of 2.7 projections per inch and an average 0.94 inch projection length. It has been found after testing that the plurality of leaf fat membrane projections 70 should be at least about 20 projections per square inch and have a length of about 0.5 inches.

The porcine leaf fat membrane 20 has draping properties that permit it to fold and exhibit a bending and shearing behavior while maintaining the ability to move freely and contour to the many different surfaces within a tissue model 66 and maintain fluidity when dissected using a surgical robot. This draping characteristic and fluidity may be imparted because the detergent solution 28 weakens the lipid structures of the porcine leaf fat tissue sample 22 and interferes with the ability of lipid hydrocarbon chains to stack on top of each other, such as may occur at colder temperatures that create a more rigid structure. The formation of micelles around different hydrocarbon tails may also take-up space and create a non-uniform membrane structure, allowing for more fluidity of the individual hydrocarbon chains of the lipid molecules than exist within the porcine leaf fat 36. It is also possible because of this fluidity to harvest the porcine leaf fat membrane 20 in one large sheet instead of numerous smaller pieces.

Because of the unique dimensions and spacing of the leaf fat membrane projections 70, it is possible to identify what type of mechanical stripping has been used to harvest the porcine leaf fat membrane 20 based on the fluidity, texture, moisture content, and nature of the leaf fat membrane projections 70. Different mechanical stripping techniques may be used besides using the edged tool 40 as described relative to FIGS. 5 and 6. Other mechanical stripping techniques may include physical stripping techniques such as centrifuging, grinding, soft abrasive blasting, scarifying, solvent stripping, or other chemical stripping and related stripping techniques.

The porcine leaf fat membrane 20 may also be stored for future use. For example, ten pieces of the harvested porcine leaf fat membrane 20 may be placed in a resealable bag with about one-half cup of the detergent solution 28 used in the initial exposure and mechanical stripping, the air removed from the bag, and then sealed. The bag may be labeled as required and the porcine leaf fat membrane 20 stored long-term for later use in surgical training with different tissue models 66.

Figure 11:
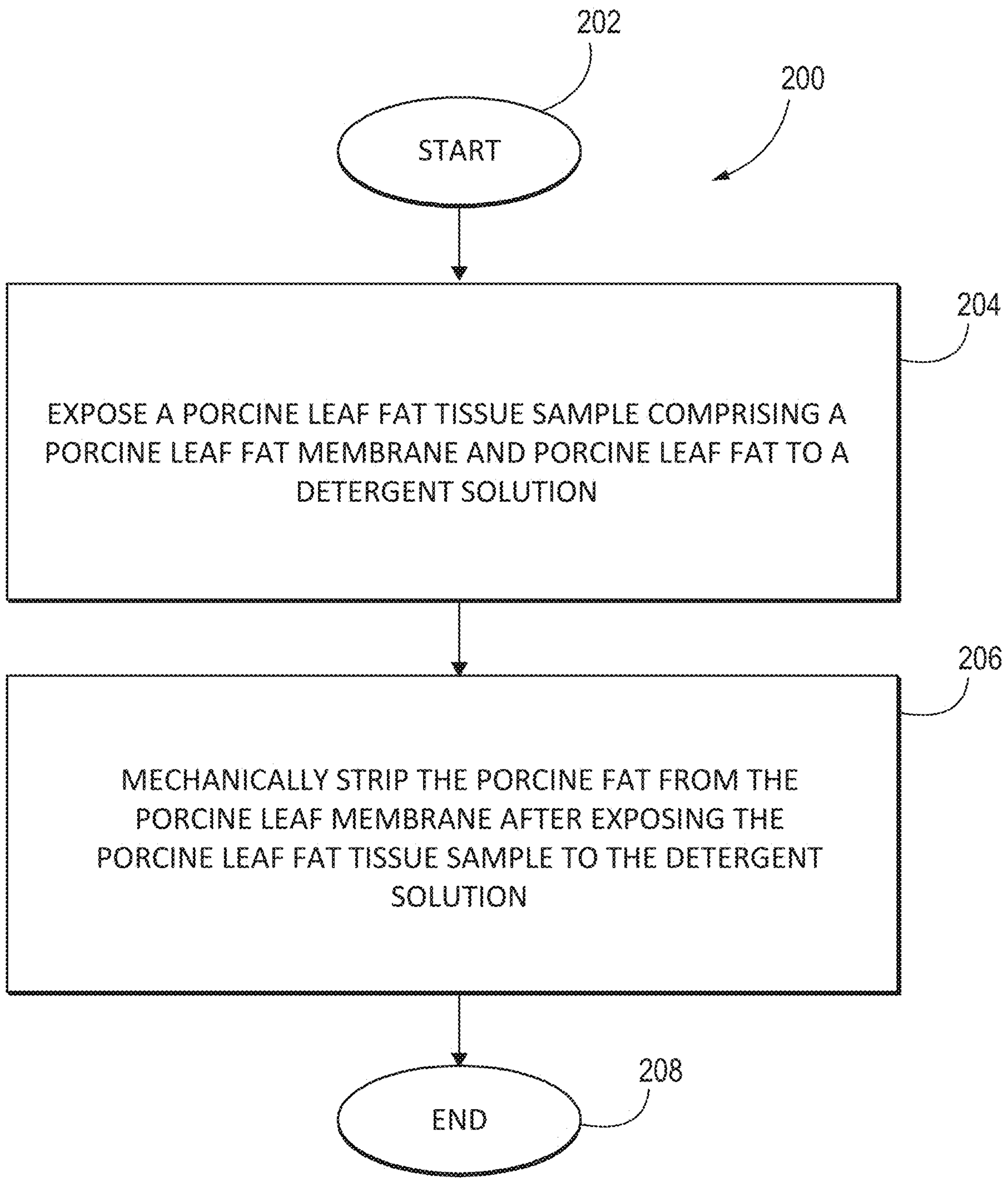
FIG. 11 is a flowchart showing a method for making the porcine leaf fat membrane.

Referring now to FIG. 11, there is illustrated generally at 200 a high-level flowchart showing a method for making the porcine leaf fat membrane 20. The process starts (Block 202) and a porcine leaf fat tissue sample 22 that includes a porcine leaf fat membrane 20 and porcine leaf fat 36 is exposed to a detergent solution 28 (Block 204). The porcine leaf fat 36 is mechanically stripped from the porcine leaf fat membrane 20 after exposing the porcine leaf fat tissue sample 22 to the detergent solution 28 (Block 206). The process ends (Block 208).

Figure 12:
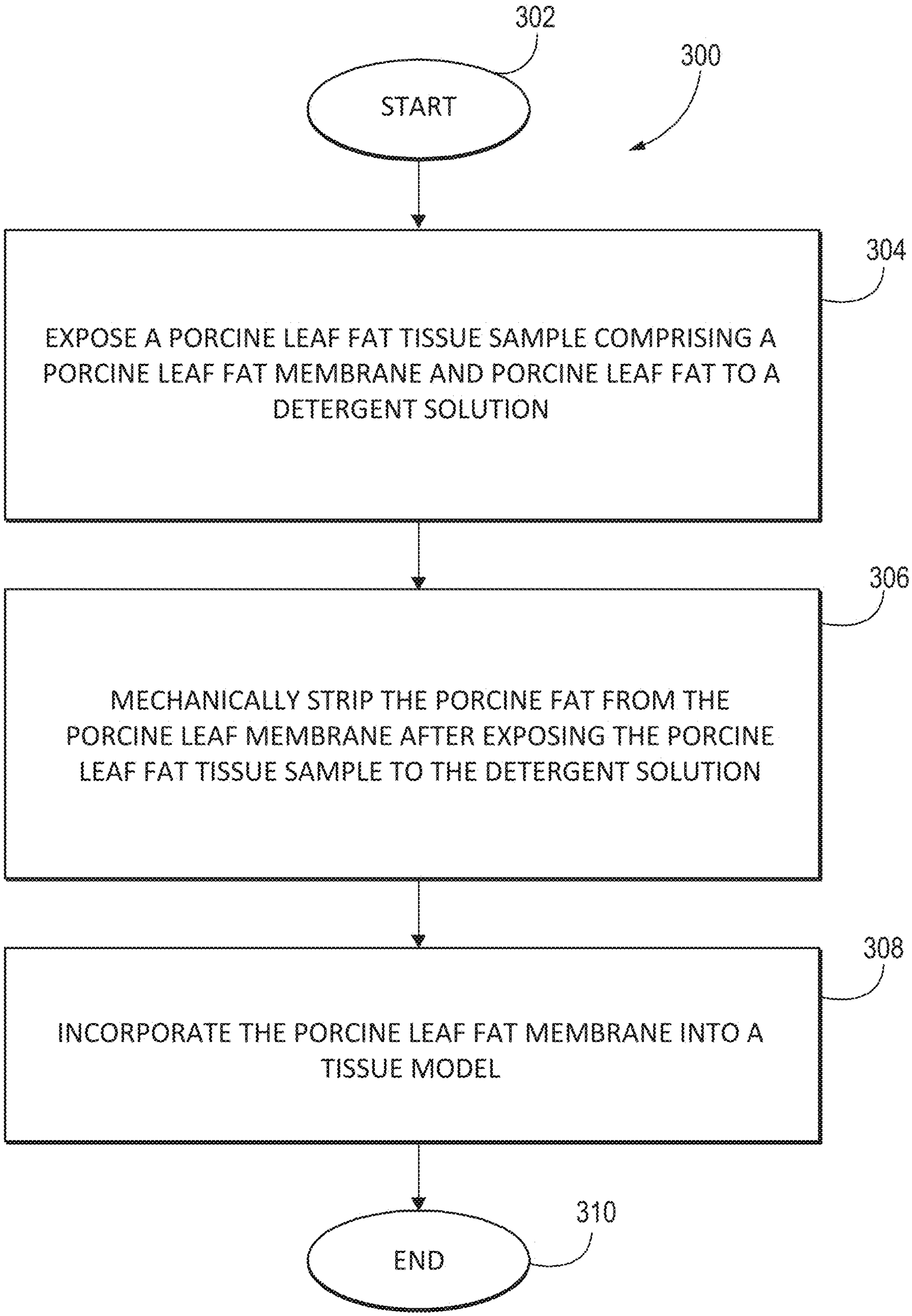
FIG. 12 is a flowchart showing a method for making a tissue model for surgical training.

Referring now to FIG. 12, a method for making a tissue model 66 for surgical training is illustrated generally at 300. The process starts (Block 302) and the method includes exposing a porcine leaf fat tissue sample 22 that includes the porcine leaf fat membrane 20 and porcine leaf fat 36 to a detergent solution 28 (Block 304). The porcine leaf fat 36 is mechanically stripped from the porcine leaf fat membrane 20 after exposing the porcine leaf fat tissue sample 22 to the detergent solution 28 (Block 306). The porcine leaf fat membrane 20 is incorporated into a tissue model 66 (Block 308). The process ends (Block 310).

The real-tissue surgical training model 100 may be used, for example, with remotely operated, computer-assisted or teleoperated surgical systems, such as those described in, for example, U.S. Pat. No. 9,358,074 (filed May 31, 2013) to Schena et al., entitled "Multi-Port Surgical Robotic System Architecture", U.S. Pat. No. 9,295,524 (filed May 31, 2013) to Schena et al., entitled "Redundant Axis and Degree of Freedom for Hardware-Constrained Remote Center Robotic Manipulator", and U.S. Pat. No. 8,852,208 (filed Aug. 12, 2010) to Gomez et al., entitled "Surgical System Instrument Mounting", each of which is hereby incorporated by reference in its entirety. Further, the real-tissue surgical training model 100 described herein may be used, for example, with a da Vinci® Surgical System, such as the da Vinci X® Surgical System or the da Vinci Xi® Surgical System, both with or without Single-Site® single orifice surgery technology, all commercialized by Intuitive Surgical, Inc., of Sunnyvale, California. Although various embodiments described herein are discussed in connection with a manipulating system of a teleoperated surgical system, the present disclosure is not limited to use with a teleoperated surgical system. Various embodiments described herein can optionally be used in conjunction with hand held instruments, such as laparoscopic tools for real-time surgical training with a harvested porcine tissue cassette.

Figure 13:
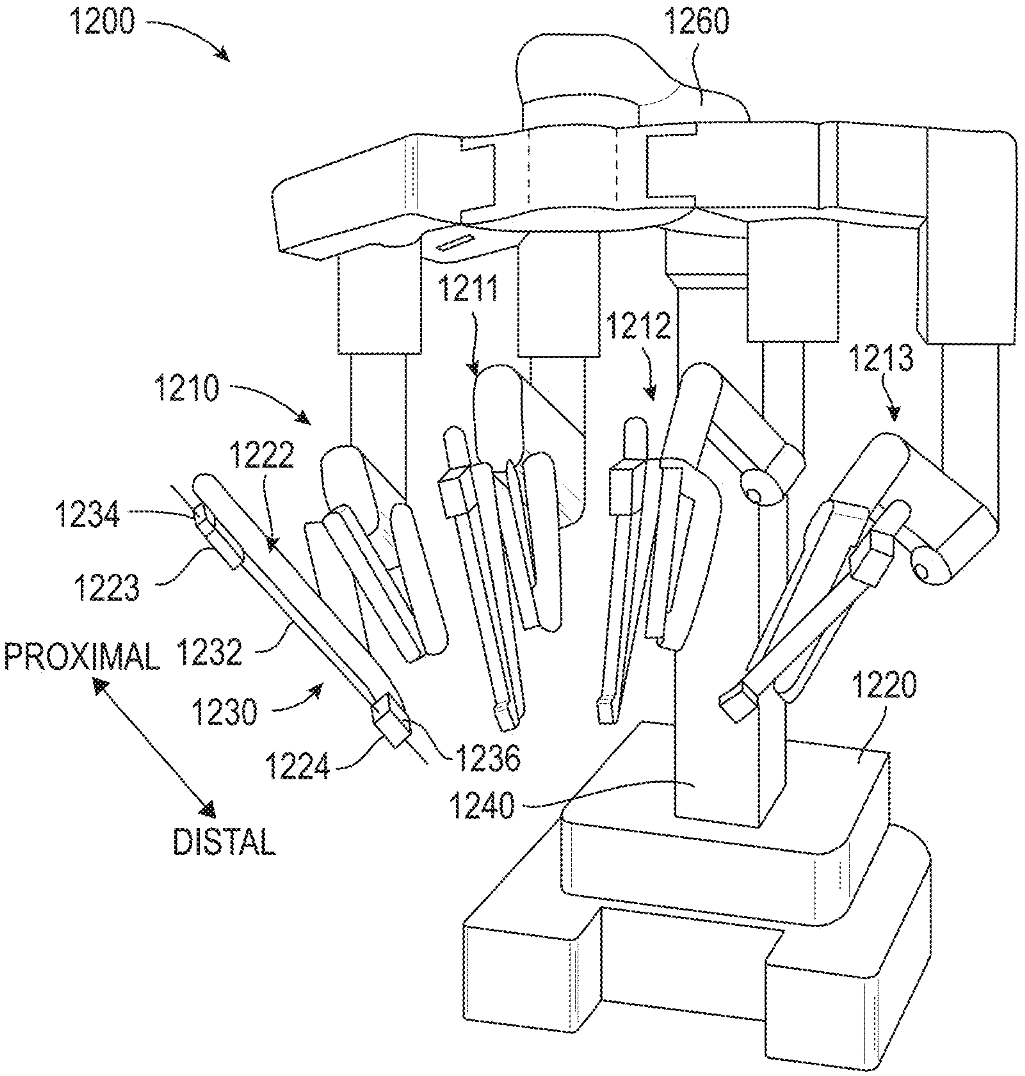
FIG. 13 is a perspective view of a manipulator system according to an example embodiment of the disclosure.

As discussed above, in accordance with various embodiments, surgical tools or instruments of the present disclosure are configured for use in teleoperated, computer-assisted surgical systems employing robotic technology (sometimes referred to as robotic surgical systems). Referring now to FIG. 13, an embodiment of a manipulator system 1200 of a computer-assisted surgical system, to which surgical instruments are configured to be mounted for use, is shown. Such a surgical system may further include a user control system, such as a surgeon console (not shown) for receiving input from a user to control instruments coupled to the manipulator system 1200, as well as an auxiliary system, such as auxiliary systems associated with the DA VINCI X® and DA VINCI XI®, Da Vinci SP.

As shown in the embodiment of FIG. 13, a manipulator system 1200 includes a base 1220, a main column 1240, and a main boom 1260 connected to main column 1240. Manipulator system 1200 also includes a plurality of manipulator arms 1210, 1211, 1212, 1213, which are each connected to main boom 1260. Manipulator arms 1210, 1211, 1212, 1213 each include an instrument mount portion 1222 to which an instrument 1230 may be mounted, which is illustrated as being attached to manipulator arm 1210.

Instrument mount portion 1222 may include a drive assembly 1223 and a cannula mount 1224, with a transmission mechanism 1234 of the instrument 1230 connecting with the drive assembly 1223, according to an embodiment. Cannula mount 1224 is configured to hold a cannula 1236 through which a shaft 1232 of instrument 1230 may extend to a surgery site during a surgical procedure. Drive assembly 1223 contains a variety of drive and other mechanisms that are controlled to respond to input commands at the surgeon console and transmit forces to the transmission mechanism 1234 to actuate the instrument 1230. Although the embodiment of FIG. 14 shows an instrument 1230 attached to only manipulator arm 1210 for ease of viewing, an instrument may be attached to any and each of manipulator arms 1210, 1211, 1212, 1213.

Other configurations of surgical systems, such as surgical systems configured for single-port surgery, are also contemplated. For example, with reference now to FIG. 14, a portion of an embodiment of a manipulator arm 2140 of a manipulator system with two surgical instruments 2300, 2310 in an installed position is shown. The surgical instruments 2300, 2310 can generally correspond to different instruments used for real-time tissue training using the harvested porcine tissue cassette. For example, the embodiments described herein may be used with a DA VINCI SP® Surgical System, commercialized by Intuitive Surgical, Inc. of Sunnyvale, California. The schematic illustration of FIG. 14 depicts only two surgical instruments for simplicity, but more than two surgical instruments may be mounted in an installed position at a manipulator system as those having ordinary skill in the art are familiar. Each surgical instrument 2300, 2310 includes a shaft 2320, 2330 having at a distal end a moveable end effector or an endoscope, camera, or other sensing device, and may or may not include a wrist mechanism (not shown) to control the movement of the distal end.

Figure 14:
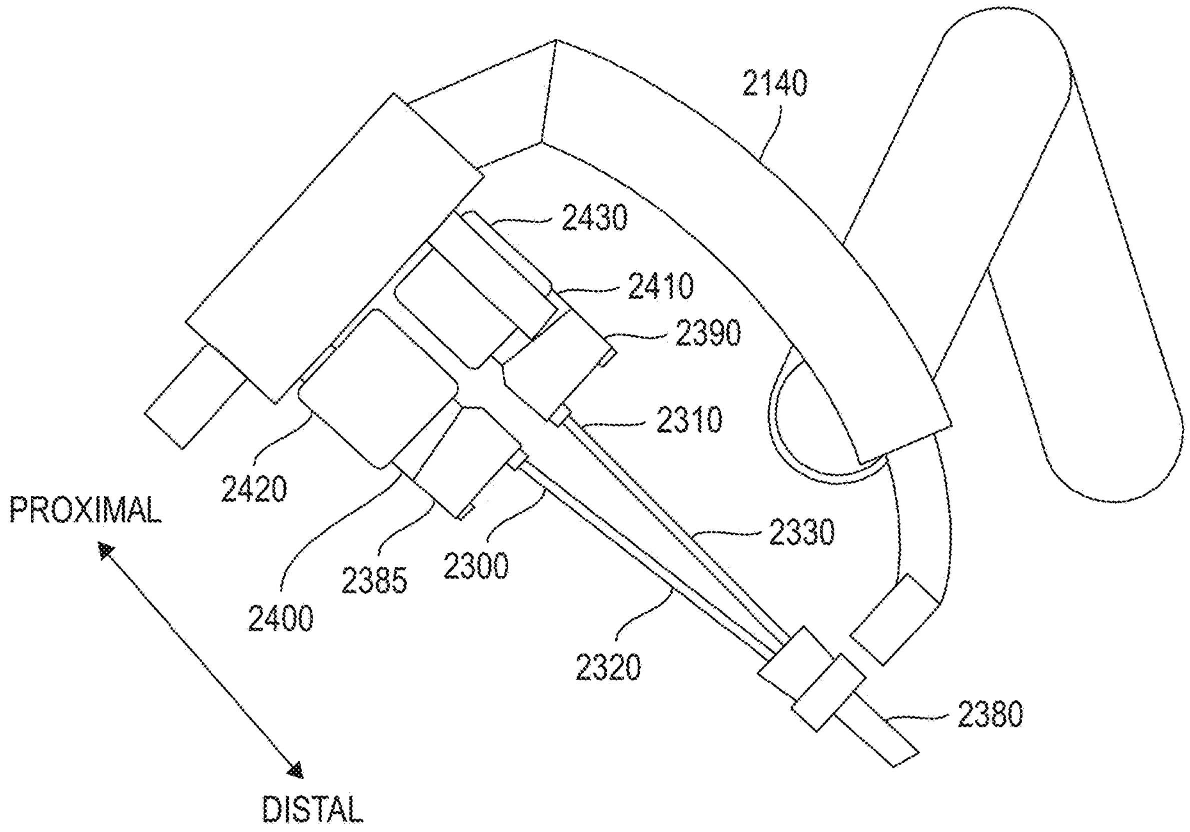
FIG. 14 is a partial schematic view of an embodiment of a manipulator system having a manipulator armed with two instruments in an installed position according to the present disclosure.

In the embodiment of FIG. 14, the distal end portions of the surgical instruments 2300, 2310 are received through a single port structure 2380 to be introduced into the harvested porcine tissue through the opening of the mouth and associated upper and lower jaws and into communication with the oropharynx region. As shown, the port structure includes a cannula and an instrument entry guide inserted into the cannula. Individual instruments are inserted into the entry guide to reach a surgical site corresponding to the oropharynx region of the porcine tissue that simulates the oropharynx region of the human body.

Other configurations of manipulator systems that can be used in conjunction with the present disclosure can use several individual manipulator arms. In addition, individual manipulator arms may include a single instrument or a plurality of instruments. Further, as discussed above, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Transmission mechanisms 2385, 2390 are disposed at a proximal end of each shaft 2320, 2330 and connect through a sterile adaptor 2400, 2410 with drive assemblies 2420, 2430, which contain a variety of internal mechanisms (not shown) that are controlled by a controller (e.g., at a control cart of a surgical system) to respond to input commands at a surgeon side console of a surgical system to transmit forces to the force transmission mechanisms 2385, 2390 to actuate surgical instruments 2300, 2310.

The embodiments described herein are not limited to the embodiments of FIGS. 13 and 14, and various other teleoperated, computer-assisted surgical system configurations may be used with the embodiments described herein. The diameter or diameters of an instrument shaft and end effector are generally selected according to the size of the cannula with which the instrument will be used and depending on the surgical procedures being performed.

This description and the accompanying drawings that illustrate various embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to another embodiment, the element may nevertheless be claimed as included in the other embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the example term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as examples. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

The invention claimed is:

1. A method for making a porcine leaf fat membrane comprising:

exposing a porcine leaf fat tissue sample to a detergent solution at a temperature range of 35° C. to 40° C. for 3 to 5 minutes, the porcine leaf fat tissue sample comprising a porcine leaf fat membrane and porcine leaf fat connected thereto; and mechanically stripping the porcine leaf fat from the porcine leaf fat membrane after exposing the porcine leaf fat tissue sample to the detergent solution for the 3 to 5 minutes that is sufficient to form a base porcine leaf fat membrane layer and a plurality of porcine leaf fat membrane projections extending therefrom, wherein the plurality of porcine leaf fat membrane projections comprise at least two projections per square inch and having a length of at least 0.5 inches, such that, the plurality of porcine leaf fat membrane projections aid in attaching components to a tissue model for surgical training.

2. The method of claim 1 wherein mechanically stripping comprises mechanically scraping with an edged tool.

3. The method of claim 2 wherein mechanically scraping comprises mechanically scraping with a fluid assist.

4. The method of claim 1 comprising sealing the porcine leaf fat membrane in a resealable bag.

5. The method of claim 4 comprising adding a portion of the detergent solution to the bag.

6. The method of claim 1 wherein the detergent solution comprises at least one of an anionic and cationic surfactant in an aqueous solution.

7. A method for making a tissue model for surgical training comprising:

exposing a porcine leaf fat tissue sample to a detergent solution at a temperature range of 35° C. to 40° C. for 3 to 5 minutes, the porcine leaf fat tissue sample comprising a porcine leaf fat membrane and porcine leaf fat connected thereto;

mechanically stripping the porcine leaf fat from the porcine leaf fat membrane after exposing the porcine leaf fat tissue sample to the detergent solution for the 3 to 5 minutes that is sufficient to form a base porcine leaf fat membrane layer and a plurality of porcine leaf fat membrane projections extending therefrom, wherein the plurality of porcine leaf fat membrane projections comprise at least two projections per square inch and having a length of at least 0.5 inches, such that, the plurality of porcine leaf fat membrane projections aid in attaching components to the tissue model; and incorporating the porcine leaf fat membrane in the tissue model.

8. The method of claim 7 wherein incorporating the porcine leaf fat membrane comprises incorporating the leaf fat membrane as a substitute for peritoneum in the tissue model.

9. The method of claim 7 wherein mechanically stripping comprises mechanically scraping with an edged tool.

10. The method of claim 9 wherein mechanically scraping comprises mechanically scraping with a fluid assist.

11. The method of claim 7 wherein the detergent solution comprises at least one of an anionic and cationic surfactant in an aqueous solution.

* * * * *